United States Patent
Buyuktimkin et al.

(10) Patent No.: US 9,821,021 B2
(45) Date of Patent: Nov. 21, 2017

(54) SENSITIZATION COMPOSITION AND METHOD OF USE

(71) Applicant: Centric Research Institute, Encinitas, CA (US)

(72) Inventors: Servet Buyuktimkin, San Diego, CA (US); Nadir Buyuktimkin, San Diego, CA (US); James L. Yeager, Lake Forest, IL (US); Albert Liu, Encinitas, CA (US)

(73) Assignee: Centric Research Institute, Encinitas, CA (US)

( * ) Notice: Subject to any disclaimer, the term of this patent is extended or adjusted under 35 U.S.C. 154(b) by 0 days.

(21) Appl. No.: 15/496,861

(22) Filed: Apr. 25, 2017

(65) Prior Publication Data
US 2017/0224755 A1    Aug. 10, 2017

Related U.S. Application Data

(63) Continuation-in-part of application No. 14/395,919, filed as application No. PCT/US2013/032371 on Mar. 15, 2013.

(60) Provisional application No. 61/638,106, filed on Apr. 25, 2012.

(51) Int. Cl.
| | | |
|---|---|---|
| A61K 36/54 | (2006.01) | |
| A61K 36/73 | (2006.01) | |
| A61K 36/00 | (2006.01) | |
| A61K 36/736 | (2006.01) | |
| A61K 36/53 | (2006.01) | |
| A61K 36/23 | (2006.01) | |
| A61K 36/738 | (2006.01) | |
| A61K 9/00 | (2006.01) | |

(52) U.S. Cl.
CPC .......... *A61K 36/736* (2013.01); *A61K 9/0034* (2013.01); *A61K 36/23* (2013.01); *A61K 36/53* (2013.01); *A61K 36/54* (2013.01); *A61K 36/738* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2009/0068128 | A1* | 3/2009 | Waddington | A61K 8/673 424/59 |
| 2010/0215775 | A1* | 8/2010 | Schmaus | A61K 8/23 424/685 |
| 2011/0086116 | A1* | 4/2011 | Florence | A61K 8/97 424/739 |

* cited by examiner

*Primary Examiner* — Chris R Tate
*Assistant Examiner* — Russell Fiebig
(74) *Attorney, Agent, or Firm* — Olson & Cepuritis, Ltd.

(57) ABSTRACT

The present invention relates to a topical composition and method of use, specifically an oil-in-water emulsion, comprised of sweet almond oil, lavender oil, rose oil, cinnamon bark oil, and coriander seed oil in a physiologically acceptable topical carrier. The composition is applied to a circumcised human penis to enhance sensitivity, preferably twice daily for a time period of at least about two weeks. Thereafter a maintenance dose can be applied once a day to maintain a desired level of sensitivity.

5 Claims, 1 Drawing Sheet

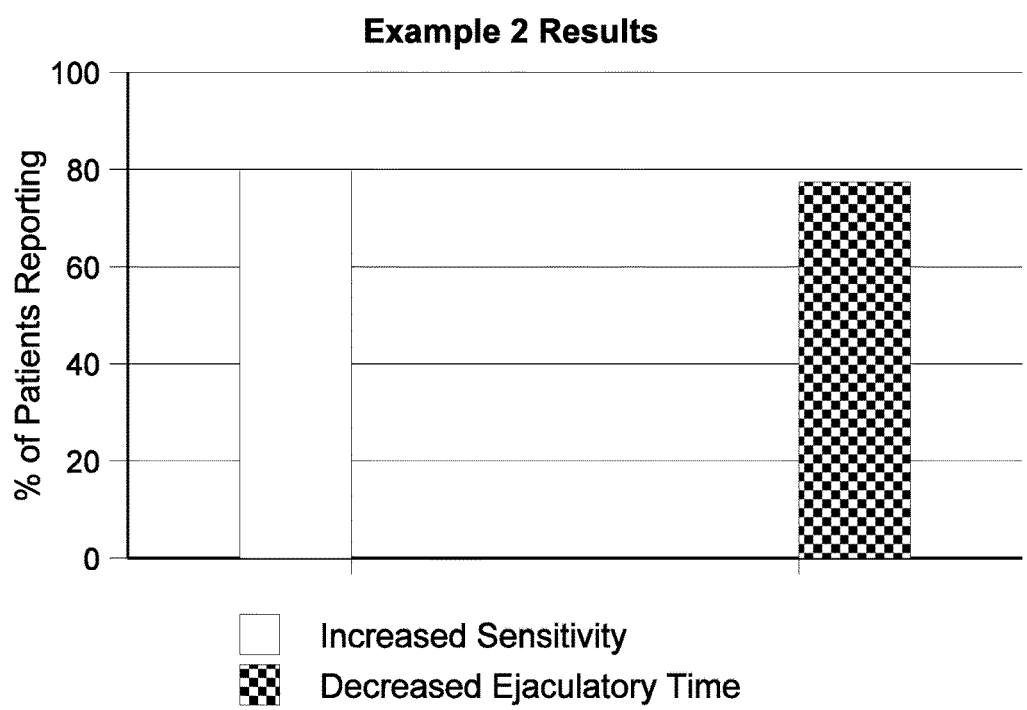
Survey Results from Example 2 Study

SENSITIZATION COMPOSITION AND METHOD OF USE

CROSS-REFERENCE TO RELATED APPLICATION

This application is a continuation-in-part of U.S. application Ser. No. 14/395,919, filed Oct. 21, 2014, which in turn is a U.S. National Stage of PCT/US2013/032371, filed on Mar. 15, 2013 and claims the benefit of U.S. Provisional Application No. 61/638,106, filed on Apr. 25, 2012, each of which is incorporated herein by reference in its entirety.

FIELD OF THE INVENTION

This invention relates generally to a non-irritating topical composition for increasing the sensitivity of the penis during sexual activity. More specifically, the invention relates to an oil-in-water emulsion for application to a circumcised penis for enhanced sensitivity.

BACKGROUND OF THE INVENTION

An intact human penis is covered by a single continuous sheath or skin system which is partly folded at different times. The folded portion of the skin system is called the foreskin or prepuce. Historically, the foreskin has been delineated as a separate anatomical structure; however, this is not correct. The foreskin is not a separate anatomical structure from the rest of the skin of the penis but rather it is the portion of the continuous skin system which happens to be folded over the glans at any given time.

Circumcision is the surgical procedure by which the foreskin is removed. Many cultures perform circumcision on infant males soon after birth; however, the procedure is also sometimes performed on adult males. Male circumcision is performed for a variety of reasons; religious, health, aesthetic, tradition, etc. Recent studies have brought into question some of the justifications for circumcision inasmuch as circumcision removes a complex, pentilaminar functional structure that contains nearly all fine touch neuroceptors of the penis and can reduce sensitivity of the glans penis to fine touch and vibration. Van Howe, Nat. Clin. Pract. Urol. 6(2):74-75 (2009).

SUMMARY OF THE INVENTION

A composition for topical application to a circumcised human penis to enhance sensitivity comprises an admixture of sweet almond oil, lavender oil, cinnamon bark oil, coriander seed oil and rose oil in a physiologically acceptable topical cream, i.e, an oil-in-water emulsion having the consistency of a viscous liquid or semi-solid.

The active ingredient, cinnamon bark oil, works by activating the Transient Receptor Potential A1 (TRPA-1) channels. TRPA-1 is involved in mechano-sensation among other actions. Activation of the TRPA-1 by cinnamon bark oil is responsible for the heat and cold sensation of the skin and results in an increase of sensation.

A method of enhancing sensitivity of a circumcised human penis comprises applying to the glans penis a therapeutically effective amount of a topical composition which comprises an admixture of sweet almond oil, lavender oil, cinnamon bark oil, coriander seed oil, and rose oil.

The term "therapeutically effective amount," as used herein and in the claims means an amount sufficient to elicit enhanced sensitivity of a human penis during sexual activity.

BRIEF DESCRIPTION OF THE DRAWINGS

FIG. 1 shows survey results from the study described in Example 2, below.

DETAILED DESCRIPTION OF PREFERRED EMBODIMENTS

The composition of the present invention is an oil-in-water emulsion comprising sweet almond oil, lavender oil, cinnamon bark oil, coriander seed oil and rose oil, preferably in a respective weight proportion of about 200:33:25:17:1. The oil-in-water emulsion is a viscous liquid or semi-solid having a cream-like consistency. The preferred dosage amount is approximately 150-300 mg of the composition per dose.

Table 1 lists the components of the composition in recommended weight percent ranges, as well as the preferred weight percent.

TABLE 1

An embodiment of the present composition

| Component | wt % | pfd wt % |
|---|---|---|
| sweet almond oil[1] | 2-10 | 6 |
| lavender oil[2] | 0.01-2 | 1 |
| rose oil[3] | 0.005-1 | 0.03 |
| cinnamon bark oil[4] | 0.01-2 | 0.1-0.75 |
| coriander seed oil[5] | 0.01-1 | 0.5 |
| sorbitol | 0.7-7 | 3.5 |
| isopropyl alcohol | 0-7 | 2.8 |
| propylene glycol | 5-25 | 20 |
| butylated hydroxytoluene | 0.01-2 | 1 |
| triethanolamine | 0.05-3 | 1 |
| benzyl alcohol | 0.01-3 | 1 |
| benzyl benzoate | 0.01-5 | 1 |
| PEG-40 hydrogenated castor oil[6] | 1-5 | 3.5 |
| acrylate/C10-30 alkyl acrylate crosspolymer[7] | 0.25-4 | 1.3 |
| disodium EDTA | 0.01-0.2 | 0.1 |
| water | q.s. to 100% | q.s. to 100% |

[1] *Prunus Amygdalus Dulcis* oil
[2] *Lavandula Angustifolia* oil
[3] *Rosa Damascena* flower oil
[4] *Cinnamomum Zeylanicum* bark oil (*Cinnamomum Verum*)
[5] *Coriandrum Sativum* seed oil
[6] Cremophor RH40
[7] Pemulen TR1

The present compositions can be prepared in a batch process as described below.

An aqueous dispersion is prepared using about 90 weight percent of required water, to which are added the acrylate crosspolymer and ethylene diamine tetraacetic acid (EDTA). EDTA can be added as the disodium salt, i.e., disodium EDTA, or as the calcium disodium salt, i.e., calcium disodium EDTA. The resulting admixture is stirred until a substantially complete dispersion is achieved usually for about two hours. A 70 weight percent solution of sorbitol in water is then added with stirring, and the stirring is continued until a substantially homogeneous composition is obtained.

A separate homogenous dispersion is prepared by admixing PEG 40-hydrogenated castor oil, benzyl alcohol, benzyl benzoate butylated hydroxytoluene, isopropanol and propylene glycol.

The prepared dispersions are then quantitatively combined in a single vessel with stirring, and the mixture of sweet almond oil, lavender oil, cinnamon bark oil, coriander seed oil and rose oil is added to the combined dispersions with stirring until a homogenous dispersion is produced. The stirring is continued for at least about one hour.

A solution of triethanolamine in the remaining ten weight percent of water is then slowly added to the produced homogenous dispersion with stirring which is continued for at least 30 minutes to produce a smooth, cream-like composition.

Example 1

A cream prepared in the foregoing manner and contained 6 weight percent sweet almond oil, 1 weight percent lavender oil, 0.03 weight percent rose oil, 0.75 weight percent cinnamon bark oil, 0.5 weight percent coriander seed oil, 3.5 weight percent sorbitol, 2.8 weight percent isopropyl alcohol, 20 weight percent propylene glycol, 1 weight percent butylated hydroxytoluene, 1 weight percent triethanolamine, 1 weight percent benzyl alcohol, 1 weight percent benzyl benzoate, 3.5 weight percent PEG-40 hydrogenated castor oil, 1.3 weight percent acrylate/C10-30 alkyl acrylate crosspolymer, 0.1 weight percent disodium EDTA. And the remainder water. The prepared cream was administered to eight circumcised male patients (age: 28 to 65 years). A dose of about 150 milligrams was applied to the glans penis twice a day for a two week period.

Six of the eight patients reported that they experienced a lasting increased sensitivity of the glans penis after the two-week treatment period.

A preferred method of use comprises application of the composition to the glans penis twice daily for at least about two weeks, preferably in an amount in the range of about 150 to about 300 milligrams per application. Thereafter a maintenance dose can be applied once a day to maintain a desired level of sensitivity.

Example 2

Patients 18 years of age and older experiencing symptoms of reduced penile sensitivity criteria were selected for enrollment. After the screening preparation, which included the collection and evaluation of the patients' sexual function information, Sensum+® cream (available from Innovus Pharmaceuticals, Inc., San Diego, Calif.) was shipped by mail to each patient. Sensum+® cream comprises: sweet almond oil, lavender oil, rose damascena flower oil, cinnamon bark oil, coriander seed oil, sorbitol, isopropyl alcohol, propylene glycol, butylated hydroxytoluene, triethanolamine, benzyl alcohol, benzyl benzoate, PEG-40 hydrogenated castor oil, acrylate/C10-30 alkyl acrylate crosspolymer, calcium disodium EDTA, hydrogenated jojoba oil, and distilled water. Cinnamon bark oil (Cinnamonum verum, Stem bark outer) was present at 0.1 weight percent. Patients were instructed to apply Sensum+® cream twice daily for the first two weeks (12 hour interval) followed by once daily for the remaining eight weeks. At the end of treatment period, patients were asked to complete efficacy questions and a safety survey. Efficacy data are presented as percent of patients who achieved improvement for penile sensitivity and who answered yes to improvement of ejaculatory time. Safety of the study was based on reported adverse events.

In this study, a total of 368 patients who met the age (18-year-old male) and symptoms of reduced penile sensitivity criteria were enrolled in this study. Clinical efficacy evaluation and safety analysis were performed for all patients who used the product. As shown in FIG. 1, survey data analyses indicate that 80% (296) of the men surveyed reported an increase in sensitivity after application of Sensum+® cream and 77.4% (285) of men reported decreased ejaculation time. There were no adverse events reported by the users or their partners.

Example 3

Patients were selected based on a survey entry questionnaire designed by Centric Research Institute (CRI) to evaluate the extent of reduced penile sensitivity on ejaculation delay in uncircumcised men with or without comorbidity of diabetes. Patients (age 18-year and older) reporting reduced penile sensitivity and delayed ejaculation (MIELT 10 minutes) were selected for enrollment. During the screening period, subjects with reduced penile sensitivity were encouraged to induce ejaculation by masturbation at three separate events with a minimum of 24 hours between each event and following the stopwatch method to establish a baseline MIELT (Masturbation-Induced Ejaculatory Latency Time). Once the enrollment period is completed, each patient was given 2 dispensers of Sensum+® cream (150 mg/pump) to apply twice daily on the glans and shaft of the penis with a 12 hour-interval between each application for 2 weeks. Subjects were instructed to abstain from any sexual activity during the first week of treatment. Subjects were asked to gather the efficacy data for penile sensitivity, overall sex life satisfaction and sexual relationship with partner at the end of the treatment period. During the second week of treatment subjects were instructed to use a stopwatch when masturbating to record the MIELT for at least 3 separate events.

The clinical variables of this study were sensitivity of the penis glans, overall sex life satisfaction, sexual relationship satisfaction with partner and Masturbation-Induced Ejaculatory Latency Time (MIELT). Changes in the penis glans sensitivity were reflected by a rating (Scale 1-10) to the question "How would you rate your penile sensitivity?" (10 being most sensitive, 1 least sensitive) at baseline and after treatment with Sensum+® cream. Answers to "How satisfied have you been with your overall sex life satisfaction?" and "How satisfied have you been with your sexual relationship with your partner?" were rated on a 1-5 scale, where 1=Very dissatisfied and 5=Very satisfied. Changes in Masturbation-Induced Ejaculation Latency Time (MIELT) at baseline and after treatment were assessed using a stopwatch method.

A total of 14 patients with reduced penile sensitivity and masturbation-induced ejaculatory latency time 10 minutes were enrolled in this study. Based on the clinical report forms (CRFs), 8 patients reported history of diabetes. Clinical efficacy evaluation and safety analysis were performed for all patients who used the product at least once. Survey data analyses indicate that at baseline, the average mean penile sensitivity was rated at 2.57±0.34 (N=14), the MIELT was 1388±125.8 seconds (N=14) and the overall sex life satisfaction and sexual relationship with partner were 1.23±0.12 (N=13). After one week treatment with Sensum+®, the mean penile sensitivity was 5.07±0.38 (N=14) (scale 1-10), the overall sex life satisfaction was 4.23±0.23 (N=13) (Scale 1-5) and the sexual relationship with partner was rated at 3.50±0.35 (N=12) (Scale 1-5). The average mean MIELT was 946.8±114.1 seconds (N=6). Statistical analysis of the mean change (Treatment baseline) for the clinical variables was statistically significant with a p value of 0.0001 for penile sensitivity, overall sex life satisfaction and sexual relationship. With respect to the MIELT, the p value was 0.0266. Reports of adverse events indicate that 14.28% (N=2) of subjects reported penile or vaginal burning.

As shown in Table 2, the results from this clinical survey study indicate that twice daily treatment for a period of two weeks with Sensum+® cream was safe and effective. Sensum+® cream improved penile sensitivity, decreased ejaculatory latency time and increased users' sex life satisfaction as well as sexual relationship with their partner.

TABLE 2

Results from Example 3 Study

|  | Baseline | Sensum+® cream | P value |
|---|---|---|---|
| Penile Sensitivity | 2.571 ± 0.3431<br>N = 14 | 5.071 ± 0.3847<br>N = 14 | <0.0001 |
| Masturbation Ejaculatory Latency Time (MELT); seconds, Mixed | 1408 ± 117.3<br>N = 6 | 946.8 ± 114.1<br>N = 6 | 0.0182 |
| Masturbation Ejaculatory Latency Time (MELT); seconds, Diabetic | 1483 ± 167.7<br>N = 4 | 986.3 ± 175.8<br>N = 4 | 0.0869 |
| Ejaculatory Time (M/IELT); seconds, Mixed | 1079 ± 110.2<br>N = 8 | 833.9 ± 102.8<br>N = 8 | 0.1257 |
| Sex Life Satisfaction | 1.231 ± 0.1216<br>N = 13 | 4.154 ± 0.2963<br>N = 13 | <0.0001 |
| Partner's Satisfaction | 1.231 ± 0.1216<br>N = 13 | 3.385 ± 0.3497<br>N = 13 | <0.0001 |

The foregoing description and the examples are intended as illustrative and are not to be taken as limiting. Still other variants within the spirit and scope of the present invention are possible and will readily present themselves to those skilled in the art.

We claim:

1. A method of enhancing sensitivity of a circumcised human penis comprising applying an effective amount of a topical composition to a glans penis in need thereof,
   wherein the topical composition comprises an effective amount of an admixture of sweet almond oil, lavender oil, cinnamon bark oil, coriander seed oil and rose oil, and
   wherein the topical composition is in the form of a physiologically-acceptable oil-in-water emulsion.

2. The method of enhancing sensitivity of a circumcised human penis in accordance with claim 1 wherein the topical composition comprises about 2 to about 10 weight percent sweet almond oil, about 0.01 to about 2 weight percent lavender oil, about 0.005 to about 1 weight percent of rose oil, about 0.01 to about 2 weight percent cinnamon bark oil, about 0.01 to about 1 weight percent of coriander seed oil, about 0.7 to about 7 weight percent sorbitol, zero to about 7 weight percent isopropyl alcohol, about 5 to about 25 weight percent of propylene glycol, about 0.01 to about 2 weight percent butylated hydroxytoluene, about 0.05 to about 3 weight percent triethanolamine, about 0.01 to about 3 weight percent benzyl alcohol, about 0.01 to about 5 weight percent benzyl benzoate, about 1 to about 5 weight percent of polyethylene glycol (40)-hydrogenated castor oil, about 0.25 to about 4 weight percent acrylate/C10-30 alkyl acrylate crosspolymer, about 0.01 to about 0.2 weight percent disodium ethylene diamine tetraacetic acid, and the remainder water.

3. The method of enhancing sensitivity of a circumcised human penis in accordance with claim 1 wherein the topical composition consists essentially of
   about 6 weight percent sweet almond oil, about 1 weight percent lavender oil, about 0.03 weight percent of rose oil, about 0.1 to 0.75 weight percent cinnamon bark oil, about 0.5 weight percent coriander seed oil, about 3.5 weight percent sorbitol, about 2.8 weight percent isopropyl alcohol, about 20 weight percent propylene glycol, about 1 weight percent butylated hydroxytoluene, about 1 weight percent triethanolamine, about 1 weight percent benzyl alcohol, about 1 weight percent benzyl benzoate, about 3.5 weight percent polyethylene glycol-(40) hydrogenated castor oil, about 1.3 weight percent acrylates/C10-30 alkyl acrylate crosspolymer, about 0.1 weight percent disodium ethylene diamine tetraacetic acid, and the remainder water.

4. The method of claim 1 wherein a dose of about 150 to about 300 milligrams of the topical composition is applied twice daily for a time period of at least about two weeks.

5. The method of claim 1 wherein a dose of about 150 to about 300 milligrams of the topical composition is applied twice daily for a time period of 14 days and thereafter once daily for a time period of 56 days.

* * * * *